United States Patent [19]
Stern et al.

[11] Patent Number: 5,583,090
[45] Date of Patent: Dec. 10, 1996

[54] HERBICIDAL MICROENCAPSULATED CLOMAZONE COMPOSITIONS WITH REDUCED VAPOR TRANSFER

[75] Inventors: Alan J. Stern, Defiance, Mo.; Alan P. Lundstedt, Cincinnati, Ohio; Salim M. Hakimi, Chesterfield; Sudabathula Rao, St. Louis, both of Mo.

[73] Assignee: Monsanto Company, St. Louis, Mo.

[21] Appl. No.: 436,751

[22] Filed: Jun. 26, 1995

[51] Int. Cl.$^6$ ............................ A01N 43/80; A01N 25/28
[52] U.S. Cl. ..................... 504/140; 504/271; 71/DIG. 1
[58] Field of Search .................................. 504/140, 271; 71/DIG. 1

[56] References Cited

U.S. PATENT DOCUMENTS

| | | | |
|---|---|---|---|
| 4,360,376 | 11/1982 | Koestler | 71/121 |
| 4,405,357 | 9/1983 | Chang | 71/88 |
| 4,936,901 | 6/1990 | Surgant, Jr. et al. | 71/92 |

Primary Examiner—S. Mark Clardy
Attorney, Agent, or Firm—Stanley M. Tarter; Arnold, White & Durkee

[57] ABSTRACT

There is provided an aqueous dispersion of microcapsules containing the herbicide clomazone dissolved in an inert high boiling organic solvent. Vapor transfer of the herbicide outside the targeted area is controlled without substantial sacrifice of the efficacy of the herbicide.

23 Claims, 1 Drawing Sheet

% Volatility Improvement

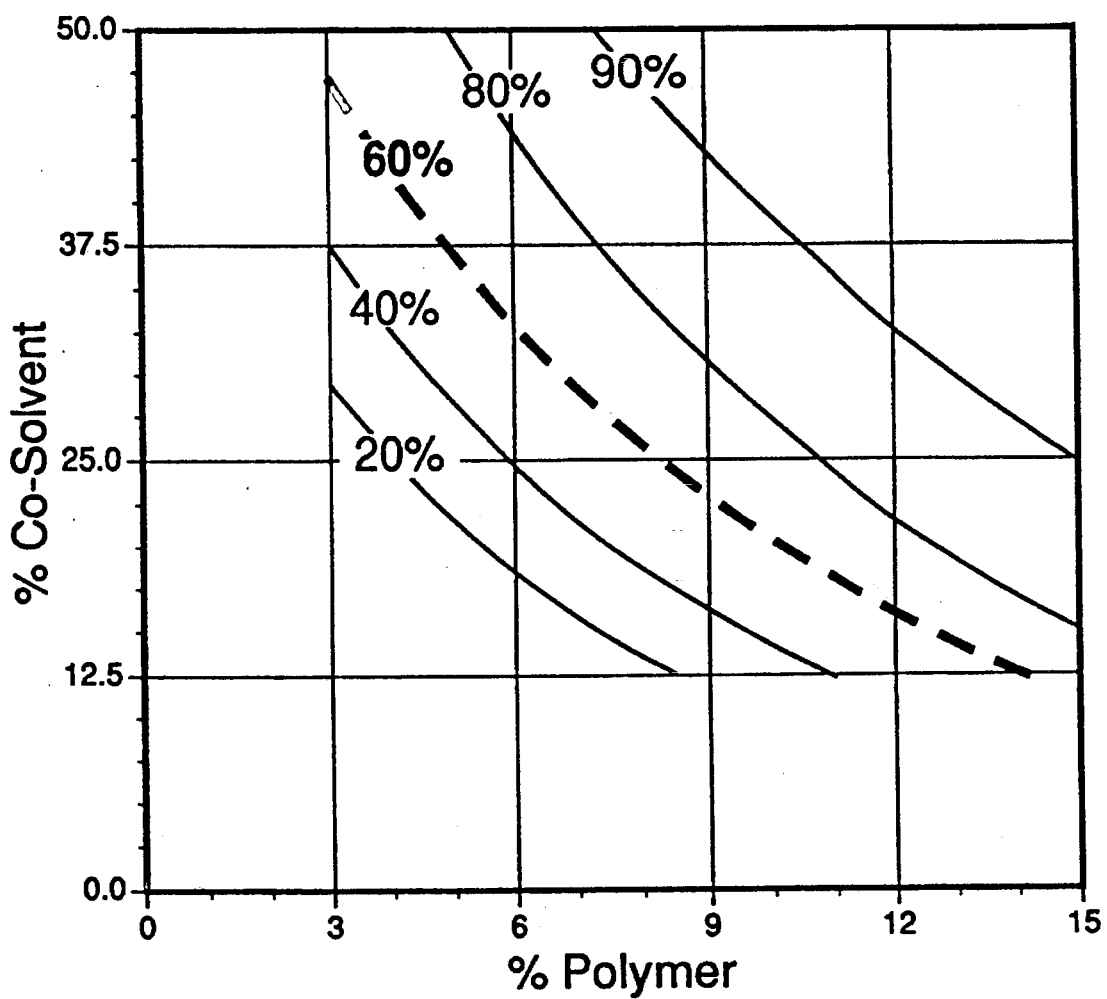

HERBICIDAL MICROENCAPSULATED CLOMAZONE COMPOSITIONS WITH REDUCED VAPOR TRANSFER

BACKGROUND OF THE INVENTION

The present invention relates to new and useful herbicidal compositions and particularly relates to herbicidal compositions requiring special precautions when being applied to reduce or prevent vapor transfer thereof to plants which are not the target of application of the compositions.

Agricultural chemicals, particularly herbicides, are sold and delivered to applicators in a wide variety of formulations, including solid formulations, such as powders, dusts and granules and time-release microcapsules, liquid formulations, such as solutions, oil concentrates, and emulsions, and suspensions of solids in liquid carriers, such as time-release microcapsules dispersed in an aqueous carrier. The choice of which type of selected formulation to be used is generally governed by many considerations, such as the physical characteristics of the active ingredients, the crop or weed species to which the formulation is to be applied, and whether the application is better made postemergence or preemergence.

Delayed-release formulations are chosen normally to provide pesticidal efficacy over an extended period of time. Microencapsulation of the pesticide is one delivery form often selected for providing the desired delayed-release. Applying microencapsulated pesticide has, in some cases, the disadvantage of substantially sacrificing the activity of the pesticide in the proper point of time.

An excellent selective soil applied herbicide commercially available for controlling many broadleaf and grass weeds, in soybean, cotton, sugarcane, rice, tobacco, oilseed rape, vegetables and others has the common name clomazone which chemically is 2-[(2-chlorophenyl)methyl]-4,4-dimethyl-3-isoxazolidinone. For brevity reasons the herbicidally active ingredient to which the present invention is concerned will be referred to herein by its common name of clomazone. Clomazone is an effective herbicide as evidenced by its ability to control, for full growing seasons and at low application rates in crops, a broad spectrum of grasses and broadleaf weeds that compete with crops. Unfortunately, clomazone is phytotoxic to some nontargeted crops and naturally occurring plant species when applied to control undesired vegetation. Contact of clomazone with such crops is the result of vapor transfer of the clomazone to sensitive species growing in adjacent areas.

Although clomazone can be, and is, sold with suitable label instructions to prevent exposure to sensitive crops, it will be evident that measures that will further decrease the exposure of the nontargeted crops to clomazone without substantial diminution of herbicidal efficacy against weeds, will greatly expand the usefulness of clomazone and thus result in lower overall costs.

Solvent-based emulsifiable concentrate (EC) formulations of clomazone may be prepared by dissolving the same in an inert organic liquid solvent, together with an appropriate emulsifier system which, when mixed with water, spontaneously forms an oil in water emulsion of the clomazone/solvent solution. Suitable solvents and emulsifiers are well known to those skilled in the art.

In conventional practice, until now, the propensity of clomazone EC to adversely affect vegetation outside the treated area has been best controlled by preplant incorporation of the herbicide into the soil. As a matter of fact, in many geographical areas, application of the herbicide by means of preplant incorporation is required to control movement of the herbicide vapors to plants outside the targeted area, where plants are sensitive to clomazone. Other restrictions on application include the use of special nozzles and the addition of drift reducing chemical agents which add to the cost of the clomazone treatment.

Preplant incorporation of a herbicide is an expensive operation requiring additional labor, fuel and land tillage to accomplish. Vapor transfer of clomazone to nontargeted sites during spraying is controlled in a limited way by careful attention to many operational parameters, including wind speed, spray pressure, droplet particle size, nozzle types and boom height. Taking the necessary precautions to minimize the off target movement of clomazone vapors is obviously an undesirable expense.

The present invention provides the art with a system for formulating and spraying of clomazone to control undesirable vegetation encountered in the cultivation of various plant species, particularly agronomic crops, while minimizing off-target vapor transfer of the herbicide. Thus, a cost effective means is provided by the practice of the present invention, wherein off-site vegetation injury is reduced while maintaining acceptable herbicidal effectiveness with surface applied clomazone-containing herbicidal compositions.

SUMMARY OF THE INVENTION

In accordance with the present invention there is provided an aqueous dispersion of microcapsules containing a herbicidally effective amount of clomazone dissolved in a suitable water-immiscible high boiling inert organic solvent. The boiling point of the solvent is, preferably, above 170° C. The encapsulant is a porous condensate polymer of polyurea, polyamide or amide-urea copolymer. To provide acceptable volatility control without unacceptable sacrifice of herbicidal efficacy, the percentage of polymer comprising the microcapsules ranges from about 3 to about 15 by weight, preferably about 5 to about 12 by weight. Also the percentage of solvent of the encapsulated material ranges from about 10 to about 50 by weight, preferably about 20 to 35 by weight. The microcapsules of the present invention provide volatility reduction of about 20–90 percent as compared with clomazone prepared and applied from an emulsifiable concentrate which is commercially available at the present time. When the composition of the present invention is sprayed or otherwise applied to the surface of soil at the proper dilution for controlling vegetation, it has been found that by encapsulating clomazone dissolved in a suitable water-immiscible inert organic solvent as described and claimed herein, clomazone may be surface-applied directly by spraying and that one may achieve effective weed control in crops without significant damage to neighboring unsprayed vegetation due to vapor transfer of the herbicide. Thus, the practice of the present invention, among other things, enables one to surface apply clomazone to control weeds in crops while eliminating or substantially diminishing the risk of clomazone injury to plant species located in areas adjacent thereto without the need to resort to expensive and time-consuming preplant incorporation or special application procedures.

BRIEF DESCRIPTION OF THE DRAWING

The accompanying drawing is a graph illustrating the percent volatility suppression improvement for microcapsules of the present invention for a range of percent of encapsulating polymer vis-a-vis a range of percent AE 700 solvent in which the encapsulated clomazone is dissolved.

DETAILED DESCRIPTION OF THE INVENTION

During the first step in preparing the formulation of the present invention, an aqueous suspension of microcapsules containing the selected clomazone organic solution is provided. The walls of the microcapsules are made of a porous polymer, such as polyurea. The microcapsule preparation comprises initially providing an aqueous solution containing an emulsifier, selected preferably from the group of the salts of ligninsulfonic acid, for example, the sodium, potassium, magnesium, and calcium, salts. Particularly effective is the sodium salt of ligninsulfonic acid. A solution of clomazone and polyfunctional polyisocyanate is added to the composition of water and lignosulfonate surfactant. The solvent in which clomazone is dissolved is a water-immiscible high boiling inert organic solvent having a boiling point, preferably, above 170° C. The resulting mixture is stirred sufficiently under suitable conditions to form a homogenous dispersion of small droplets of the pesticide within the aqueous phase.

Thereafter, a polyfunctional amine is added with the stirring being continued until the polyfunctional amine has essentially fully reacted with the polyfunctional isocyanate. The polyfunctional isocyanate and the polyfunctional amine react in the presence of the surfactant under proper agitation and reaction conditions to form microcapsules having polyurea walls encapsulating the herbicide. The rate of the polymerization will depend on the reaction conditions employed. The rate of polymerization will generally be directly related to the temperature at which the reaction takes place.

The encapsulation process of the present invention is capable of satisfactory performance and production of encapsulated material without adjustment to a specific pH value. That is, as a rule no adjustment of the pH of the system need be made during the encapsulation process. If it is desired to adjust the pH of the finished microcapsule formulation as, for example, when the aqueous base formulation of the microcapsules is combined with other herbicides, fertilizers, etc., conventional and suitable reagents for pH adjustment may be used. Such reagents include hydrochloric acid, acetic acid, phosphoric acid, sodium hydroxide, potassium hydroxide, etc.

The agitation employed to establish the dispersion of water immiscible phase droplets in the aqueous phase during the production of the formulation of the present invention may be supplied by any means capable of providing suitable high shear. That is to say that any variable shear mixing apparatus, e.g., a Waring Blender, a Brinkman Polytron homogenizer, Ross Model 100L homogenizer and the like can be usefully employed to provide the desired shear.

The particular size of the microcapsules for formulating the composition of the present invention will range from about one micron up to about one hundred microns in average diameter. From about one to about twenty microns is a preferred average range. The size distribution of the microcapsules is not of critical importance.

Among suitable water-immiscible highly boiling inert organic solvents in which clomazone is dissolved are mixtures of mono- and polyalkylated aromatics commercially available from Shell Oil Co. under the trademark SHELLSOL, various petroleum fluids available from Exxon such as Aromatic 200, AE700, and Exxate 700, various fatty acid methyl esters available from Henkel Corporation, such as Emery 2209, Emery 2270, and Emery 2301. The selected organic solvent has a boiling point above 170° C.

The homogenous dispersions of polymer microencapsulated pesticides in water with an effective emulsifier, such as lignosulfonate prepared in the first step, may be blended with a suspension system composition. The suspension system composition may comprise a combination of agents, such as surfactants, dispersants, antifreeze agents, clays, water, salts, polymers, and other suspension stabilizing and density balancing agents, appropriately selected to keep the microcapsules in stable homogeneous suspension in the water-based carrier over an extended period of time as long as for example two years or more. The agents comprising the suspension system will generally comprise 1 percent by weight to 15 percent by weight of the formulation and preferably 2 percent by weight to 10 percent by weight.

A wide range of such agents may be used, and the optimum combination for each particular suspension system of active ingredient will vary. Suitable clays include bentonite clay and attapulgite clay and mixtures thereof, preferably in the range from about 0.01% to about 1.0% solid by weight, relative to the total formulation weight although greater or lesser amounts may be employed. The presence of at least one clay conventionally used in suspension systems improves the stability of the suspended microcapsules and particularly aids in the redistribution of the microcapsules upon shaking in the event some settling of microcapsules is experienced and redistribution thereof is required.

Another preferred suspension system may also include a small amount of a xanthan gum thickening agent to aid in stabilizing the suspension of the microcapsules. The gum is preferably present in an amount in the range from about 0.01 percent by weight to about 0.1 percent by weight although greater or lesser amounts may be employed.

In the preferred final product about 100 to 750 grams of microcapsules (polymer plus encapsulated material) per liter of the composition and more preferably about 400 to about 600 grams microcapsules per liter are present. The encapsulating polymer component to the encapsulated pesticide normally will be in the range of about 0.02 percent by weight to about 5.0 percent by weight and preferably in the range of about 0.04 percent by weight to about 4.0 percent by weight.

Within the scope of this invention, polyisocyanates will be generally understood as meaning those compounds that contain two and more isocyanate groups in the molecule. Preferred isocyanates are di- and triisocyanates whose isocyanate groups may be linked to an aliphatic or aromatic moiety. Examples of suitable aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate. Suitable aromatic isocyanates are toluene diisocyanate (TDI: DESMODUR Registered TM VL, Bayer), polymethylene polyphenylisocyanate (MONDUR Registered TM MR, Miles Chemical Company); PAPI Registered TM, PAPI Registered TM 135 (Upjohn Company), 2,4,4'-diphenyl ether triisocyanate, 3,3'-dimethyl-4,4'-diphenyl diisocyanate, 3,3'-dimethoxy-4,4'diphenyl diisocyanate, 1,5-naphthalene diisocyanate and 4,4',4"-triphenylmethane triisocyanate. A further suitable diisocyanate is isophorone diisocyanate. Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked urethane groups to the polyhydric alcohol to form high molecular polyisocyanates. Another suitable product of this kind (DESMODUR Registered TM L) can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenylisocyanate.

The di- and triisocyanates specified above can be employed individually or as mixtures of two or more such isocyanates.

Suitable polyamines within the scope of this invention will be understood as meaning in general those compounds that contain two or more primary amino groups in the molecule, which amino groups maybe linked to aliphatic and aromatic moieties.

Examples of suitable aliphatic polyamines are alpha, omega-diamines of the formula $H_2N(CH_2)_nNH_2$ wherein n is an integer from 2 to 6. Exemplary of such diamines are ethylenediamine, propylene-1,3-diamine, tetramethylenediamine, pentamethylenediamine and hexamethylenediamine. A preferred diamine is hexamethylenediamine.

Further suitable aliphatic polyamines are polyethyleneamines of the formula $H_2N(CH_2CH_2NH)_nH$ wherein n is an integer from 2 to 5. Representative examples of such polyethyleneamines are: diethylenetriamine, triethylenetriamine, tetraethylenepentamine, pentaethylenehexamine.

Examples of suitable aromatic polyamines are 1,3-phenylenediamine, 2,4-toluylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetraaminoanthraquinone. Those polyamines which are insoluble or insufficiently soluble in water may be used as hydrochloride salts.

Yet further suitable polyamines are those that contain sulfo or carboxyl groups in addition to the amino groups. Examples of such polyamines are 1,4-phenylene diaminesulfonic acid, 4,4'-diaminodiphenyl-2-sulfonic acid, or diaminoammocarboxylic acids such as ornithene and lysine.

Suitable liquid fertilizers can be mixed with the formulations herein without the formation of unacceptable amounts of agglomerates in the spray tank, thus avoiding poor spraying performance. The liquid fertilizers used in mixtures of the present invention can be liquid nitrogen fertilizers, optionally containing phosphate and/or potash components. Liquid fertilizers are usually designated by the percentage weight of nitrogen, phosphorous and potassium (N-P-K) ratios, e.g., 4-10-10, 6-18-18, or 10-30-10.

The present invention is better illustrated and is explained in more detail in the following examples wherein parts and percentages are given on a weight basis unless otherwise stated. It should be understood that the examples are merely illustrative of the invention and not limitative.

EXAMPLE I

This example illustrates the preparation of an aqueous suspension of microencapsulated clomazone solution. In the microencapsulation operation, microcapsules containing a solution of clomazone and AE700 solvent were prepared from the following components.

TABLE 1

| Component | Parts |
| --- | --- |
| Clomazone (Technical)[1] | 97.5 |
| AE700[2] | 97.5 |
| PAPI 2027[3] | 20.4 |
| HMD[4] | 20.4 |
| REAX 88B[5] | 145.7 |
|  | 381.5 |

1. 90% active ingredient.
2. Aromatic ester solvent obtained from Exxon Chemical which chemically is identified as 1,2-benzenedicarboxylic di ($C_6$–$C_8$), branched alkyl ester.
3. Polymethylene polyphenylisocyanate produced by Dow Chemical having an average functionality of 2.7 and a typical isocyanate equivalent weight of 134.
4. Hexamethylenediamine (43% aq. sol.).
5. Na salt of ligninsulfonic acid (3.0% aq. sol.).

Appropriate amounts of PAPI, clomazone, and AE700 solvent were stirred together to form a uniform liquid mixture. In a Waring blender cup containing the REAX 88B solution preheated to about 50° C., the shear was gradually increased with concurrent addition of the PAPI-clomazone-AE700 solvent mixture to form a uniform emulsion. The higher level of shear was continued for about 30 seconds. Thereafter, the shear was reduced to an intermediate level that was about one-half of the initial level, and the HMD component was added while maintaining this intermediate shear, whereupon microcapsules of diameters in the range of 2 to 20 microns on an average in an aqueous suspension were formed. The walls of the microcapsules were made of polymeric urea and encompassed the clomazone-containing solution. Sixty seconds after the HMD addition was completed, the shear was reduced to a low level which provided shear sufficient to maintain continuous agitation. This microencapsulated feedstock was allowed to cool at low shear under ambient conditions for about 30 minutes before subsequent components were added.

In the blending and suspension operations, 37 parts of sodium nitrate and 2.2 parts of 48.5 percent aluminum sulfate as densification salts were added to the microencapsulated feedstock at low shear to form a microcapsule-containing aqueous suspension. The nitrate salt significantly enhanced the density of the aqueous phase of the product. Finally, 13 parts of an aqueous solution containing 1.5 percent xanthan gum thickener (Keltrol RD) and a biocidal amount of Legend biocide were added to the densified aqueous suspension. After maintaining low shear agitation for an additional 10 minutes, the resulting product was allowed to cool to room temperature. The formulation was characterized as having 12 percent polymer, 22.5 percent solvent and 22.5 percent clomazone.

EXAMPLE II

Additional formulations were prepared in accordance with Example I, except that various combinations of percent polymer and percent encapsulated herbicide solution were used as set out in Table 2 below. The formulation of Example 1 is identified as Sample ID 9 in the table.

TABLE 2

| Sample ID | % Polymer | % AE700 Solvent | % Clomazone |
| --- | --- | --- | --- |
| 1 | 3 | 25.0 | 31.1 |
| 2 | 3 | 37.5 | 25.8 |
| 3 | 3 | 50.0 | 20.6 |
| 4 | 7 | 12.5 | 36.1 |
| 5 | 7 | 25.0 | 31.1 |
| 6 | 7 | 37.5 | 25.8 |
| 7 | 7 | 50.0 | 20.6 |
| 8 | 11 | 12.5 | 36.1 |
| 9 | 11 | 25.0 | 31.1 |
| 10 | 11 | 37.5 | 25.8 |
| 11 | 15 | 12.5 | 35.7 |
| 12 | 15 | 25.0 | 30.6 |
| 13 | 15 | 37.5 | 25.5 |
| 14 | 15 | 50.0 | 20.5 |

It was noted that the resulting samples were homogenous suspensions.

EXAMPLE III

This example illustrates the method used to quantify off-site injury of neighboring vegetation due to vapor drift of clomazone and bioefficacy or weed control of example formulations.

Square plots with 20-foot (7.1 meter) sides were planted at least two weeks prior to chemical application with a species known to be sensitive to clomazone bleaching, namely wheat. A 22-inch (0.56 meter) diameter circle in the center of each plot, designated the target application area, was hand-weeded and watered just prior chemical application to provide a wet, bare soil surface. A circular 32-gallon (121 liter) plastic barrel with its bottom and top removed was then placed vertically on the target application area.

A spray solution was prepared by diluting the test formulation with water such that 220 gallons per acre (2056 liters per hectare) were applied through a single nozzle at 20 psi (138 kilo Pascals) at a rate of 2.24 kilograms per hectare. The spray solution was applied to the soil surface inside the barrel. Before removing the barrel, a waiting period of one minute transpired to assure that all spray droplets have settled to the ground.

At various times from three to fourteen days after treatment, measurements were taken of the distance from the outer edge of the target application circle to the location of a herbicidally vapor transfer affected plant observed to be farthest from the edge of the clomazone treated circle.

To compare the percent volatility suppression improvement obtained by the practice of the present invention, various formulations of Example II were evaluated by the just-described test procedure against commercially obtained COMMAND® 4EC herbicide composed of 47 percent clomazone and 53 percent inerts formulated as an emulsifiable concentrate in side-by-side tests. The improvement in percent vapor transfer reduction (VTR) is seen in Table 3 below.

To compare bioefficacy or weed control of examples, an area of 4.5 square meters was treated with a rate of 0.84 kilograms per hectare of clomazone contained in each example. Three replicates of each example were observed for weed control or bioefficacy by observing the percentage of undesirable species which emerged in these plots after application of the example formulas as compared to an untreated control.

Percent (VTR) is determined by the following equation.

$$\% VTR = 100 - \frac{\text{maximum distance of off-site movement of new formulation}}{\text{maximum distance of off-site movement of COMMAND EC}} \times 100$$

TABLE 3

| Sample ID | Distance | % Vapor Transfer Reduction | % Bioefficacy |
| --- | --- | --- | --- |
| Command 4EC | 100 | 0 | 74.5 |
| 1 | 88 | 12 | 84.0 |
| 2 | 64 | 36 | 78.5 |
| 3 | 36 | 64 | 77.5 |
| 4 | 95 | 5 | 84.0 |
| 5 | 60 | 40 | 76.0 |
| 6 | 25 | 75 | 65.0 |
| 7 | 10 | 90 | 52.0 |
| 8 | 72 | 28 | 78.0 |
| 9 | 18 | 82 | 65.0 |
| 10 | 5 | 95 | 51.5 |
| 11 | 43 | 57 | 70.0 |
| 12 | 6 | 94 | 39.5 |
| 13 | 6 | 94 | 28.5 |
| 14 | 0 | 100 | 35 |

With reference to the drawing, it is noted that a 40 percent improvement in VTR can be obtained when the microcapsules are composed of 6 percent polymer and the encapsulated clomazone solution contains about 25 percent organic solvent as compared to the use of the commercial EC product with good weed control being obtained. A 75 percent VTR with acceptable weed control can be obtained when the microcapsules are composed of 12 percent polymer and the encapsulated clomazone solution contains 21 percent organic solvent. A 90 percent VTR can be obtained when the microcapsules were composed of 9 percent polymer and the encapsulated clomazone solution contained 43 percent solvent but the weed control level was significantly reduced.

With reference to the drawing, it is seen that as compared to the use of the commercial EC product, about 50 percent improvement in VTR is achieved while maintaining good weed control when the microcapsules are composed of 3 percent polymer and 40 percent solvent. About 50 percent VTR with acceptable weed control is obtained when the microcapsules are composed of 7 percent polymer and the encapsulated clomazone solution contains 25 percent organic solvent (Sample 6). A 95 percent VTR is obtained when the microcapsules are composed of 11 percent polymer and the encapsulated clomazone solution contains 37.5 percent solvent (Sample 10), but the weed control level is reduced.

In the above examples of the present invention, REAX 88B lignosulfonate surfactant was obtained from Westvaco Corporation and had a nominal degree of sulfonation of about 3.8. The sulfonic acid groups were located both on aromatic ring and aliphatic side chains.

Legend MK biocide was obtained from Rohm and Haas as a mixture of two isothiazolones as the active ingredients, namely 5-chloro-2-methyl-4-isothiazolin-3-one- and 2-methyl-4-isothiazolin-3-one.

The xanthan gums were obtained from Merck & Co., Inc., under the names KELZAN S and Keltrol RD in the form of a dry powder.

Similar excellent results as obtained in the above examples can be obtained when different polyurea-forming substances, different suspending aids and other solvents salts are employed. For example, the urea polymer can be formed by the hydrolysis of an isocyanate monomer to form an amine which, in turn, reacts with another isocyanate monomer to form polyurea.

Although the above examples illustrate the use of lignosulfonate as a preferred surface active agent in the microencapsulation step, other known surface active agents can also be used, for example, the sodium salt of alkylnaphthalene sulfonic acid, the potassium salt of alkylnaphthalene sulfonic acid, salts of polystrenesulfonic acid, in particular, the alkali metal, alkaline earth metal and ammonium salts thereof, and salts of condensates of napthalenesulfonic acids, etc., and mixtures thereof. The dispersant system for the microencapsulation process may also optionally contain one or more non-ionic surfactant, non-ionic protective colloid, or a cationic component.

Ordinarily, the formulations may be applied without further dilution or as dilute suspensions in water or other suitable diluent. The compositions may be applied to the area wherein control is desired, prior to or after emergence in the case of agronomic crops, by spraying onto the surface of the soil in the case of liquid compositions. The user may, if desired, blend the clomazone formulation into the upper layer of soil by cultivation.

Clomazone may be formulated and/or applied together with other herbicides compatible therewith insecticides, fungicides, nematocide, plant growth regulators, safeners, fertilizers, and other agricultural chemicals. In applying the other active compounds with the formulation of this invention, whether formulated alone or with other agricultural chemicals, an effective amount of each active ingredient is employed. The amount constituting an effective amount is variable, depending on the ratio of added ingredients to clomazone and other factors, such as the type of soil, the expected pattern of rainfall or irrigation, the plant species to be controlled, and the crop, if any, to be grown. Generally, a uniform application of from about 0.01 to about 2.0 kilogram per hectare of clomazone will be employed, more preferably about 0.3 to about 1.5 kilogram per hectare. Generally, the rate of application of clomazone in the field will be about two to four times that in the greenhouse. Acetochlor, alachlor and metolachlor are preferred herbicides for forming mixtures with clomazone.

As can be seen above, by the practice of the present invention one can reduce off-site injury to plants while maintaining the herbicidal effectiveness of a surface-applied clomazone.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and description set forth hereinabove; but rather it is understood that the claims are to be construed as encompassing all the features of patentable novelty which reside in the present invention as described herein, including all features which would be treated as equivalents thereof by those skilled in the art to which the invention pertains.

What is claimed:

1. A sprayable herbicidal formulation comprising an aqueous liquid having suspended therein a multitude of solid microcapsules having a capsule wall of a porous polymer encapsulating clomazone dissolved in a high boiling inert organic solvent, about 3 percent by weight to about 15 percent by weight of the microcapsules being composed of the said polymer and about 10 percent by weight to about 90 percent by weight of the encapsulated solution being comprised of the organic solvent, whereby when said formulation is sprayed onto one plot containing vegetation, vapor transfer of the herbicide to a nearby plot containing vegetation is effectively suppressed without substantial sacrifice of herbicidal efficacy of the herbicide in the plot to which the spray is applied.

2. The formulation of claim 1 wherein the polymeric encapsulant comprises about 5 percent by weight to about 12 percent by weight of the microcapsules.

3. The formulation of claim 1 wherein 20 percent by weight to 35 percent by weight of the encapsulated material by weight is comprised of the organic solvent.

4. The formulation of claim 1 wherein the polymer is a polyurea.

5. The formulation of claim 2 wherein the polyurea is the polymerization product of a polyisocyanate and a polyamine.

6. The formulation of claim 3 containing a suspension system to inhibit the microcapsules from settling.

7. A method of controlling vegetation comprising:

a) preparing a formulation comprising an aqueous liquid having suspended therein a multitude of solid microcapsules having a capsule wall of a porous polymer encapsulating clomazone dissolved in an organic solvent, about 3 percent by weight to about 15 percent by weight of the microcapsules being comprised of the said polymer and about 10 percent by weight to about 50 percent by weight of the encapsulated solution being comprised of the organic solvent; and b) spraying the aqueous liquid to apply the clomazone in a herbicidally effective amount to the surface of a selected plot containing vegetation to be controlled, whereby vapor transfer of the sprayed herbicide to a nearby plot containing vegetation is effectively suppressed without substantial sacrifice of the herbicidal efficacy of the herbicide in the plot to which the formulation is sprayed.

8. The formulation of claim 7 wherein the polymeric encapsulant comprises about 5 percent by weight to about 12 percent by weight of the microcapsules.

9. The method of claim 8 wherein 20 percent by weight to 30 percent by weight of the encapsulated material by weight is composed of an organic solvent.

10. The method of claim 5 wherein the polymer is polyurea.

11. The method of claim 6 wherein the polyurea is the polymerization product of a polyisocyanate and a polyamine.

12. The formulation of claim 1 wherein said formulation further comprises a suspension system comprising a surfactant and a stabilizing agent.

13. The formulation of claim 12 wherein the agents in the suspension system comprise 1 percent by weight to 15 percent by weight of the formulation.

14. The formulation of claim 12 wherein the agents in the suspension system comprise 2 percent by weight to 10 percent by weight of the formulation.

15. The formulation of claim 12 wherein the surfactant is a lignosulfonate.

16. The formulation of claim 12 which contains a gum in an amount of from about 0.01 percent by weight to about 0.1 percent by weight.

17. The formulation of claim 12 which contains a fertilizer.

18. The formulation of claim 12 which contains a nitrate densification agent.

19. The formulation of claim 1 wherein the organic solvent has a boiling point above 170° C.

20. The formulation of claim 12 wherein the stabilizing agent is clay.

21. A sprayable herbicidal formulation having reduced vapor transfer without substantial sacrifice of herbicidal activity comprising:

a) An aqueous liquid having suspended therein about 400 to 600 grams per liter solid microcapsules having a capsule wall of a porous polyurea polymer encapsulating clomazone dissolved in 1, 2-benzenedicarboxylic di($C_6$–$C_8$) branched alkyl ester solvent, said polymer being the polymeric reaction product of hexamethylenediamine and polymethylene polyphenzlisocyante, about 3 percent by weight to about 15 percent by weight of the microcapsules being composed of said polymer and about 10 percent by weight to about 90 percent by weight of the encapsulated solution being comprised of the said solvent; and b) a microcapsule suspension system comprising (i) a lignosulfonate surfactant, and (ii) a stabilizing clay.

22. The herbicidal formulation of claim 21 wherein clomazone is combined with with a second herbicide selected from the group of alachlor, acetochlor, and metolachlor.

23. A method of controlling vegetation comprising spraying the herbicidal formulation of claim 21 to apply clomazone to the vegetation at the rate of about 0.01 to about 2.0 kilograms per hectare.

* * * * *